United States Patent [19]

Goel et al.

[11] Patent Number: 4,477,385

[45] Date of Patent: Oct. 16, 1984

[54] MANUFACTURE OF HIGHER ARYL ESTERS

[75] Inventors: Anil B. Goel, Worthington; Michael E. Pettiford, Columbus, both of Ohio

[73] Assignee: Ashland Oil, Inc., Ashland, Ky.

[21] Appl. No.: 463,164

[22] Filed: Feb. 2, 1983

[51] Int. Cl.³ ...................... C07C 67/04; C07C 67/38
[52] U.S. Cl. .............................. 260/410.9 R; 260/406; 260/410.5
[58] Field of Search ............. 260/410.9 R, 406, 410.5; 560/131

[56] References Cited

U.S. PATENT DOCUMENTS

| | | | |
|---|---|---|---|
| 3,493,605 | 2/1970 | Selwitz | 260/410.5 |
| 3,646,111 | 2/1972 | Hörnig et al. | 560/131 |
| 3,651,127 | 3/1972 | Hörnig et al. | 560/131 |
| 3,772,383 | 11/1973 | Kominami et al. | 560/131 |
| 4,229,587 | 10/1980 | Murib | 560/131 |

*Primary Examiner*—Y. Harris-Smith
*Attorney, Agent, or Firm*—John F. Jones

[57] ABSTRACT

The oxidation process for the manufacture of higher aryl esters comprising contacting the reaction mixture of a higher aromatic hydrocarbon, an organic solvent, a carboxylic acid and molecular oxygen in the liquid phase at an elevated temperature with a catalyst composed of palladium or a compound of palladium, an antimony compound and a compound of at least one member selected from the group consisting of alkali metals and alkaline earth metals is described.

13 Claims, No Drawings

MANUFACTURE OF HIGHER ARYL ESTERS

This invention is an improvement over the process more fully described and claimed in the copending U.S. patent application Ser. No. 348,561, filed Feb. 12, 1982, by Anil B. Goel and Robert A. Grimm. The use of organic solvents in the manufacture of higher aryl esters is also described in the copending U.S. patent application of Anil B. Goel, Ser. No. 416,809, filed Sept. 13, 1982.

BACKGROUND OF THE INVENTION

1. Field of the Invention

The present invention provides an improved process for making aryl esters from higher aromatic hydrocarbon compounds such as naphthalene, anthracene, biphenyl, phenanthrene, fluorene, terphenyls, and the like, which comprises reacting a mixture of the higher aromatic hydrocarbon, a hydrocarbon solvent, molecular oxygen and a higher carboxylic acid in the liquid phase in the presence of a catalyst which is composed of palladium or a compound of palladium, a compound of antimony and a compound of at least one metal selected from Group I and Group II of the Mendeleev Periodic Table of Elements.

2. Description of the Prior Art

The manufacture of phenol by the direct oxidation of benzene with oxygen is known. There are, for instance, thermal processes which are performed at very high temperatures in which the phenol formed is susceptible to further oxidation so that considerable loss of yield occurs as is disclosed in U.S. Pat. No. 2,223,383. In the presence of catalysts, the oxidation can be carried out at somewhat lower temperatures as in U.S. Pat. No. 3,133,122 but the reactions have been plagued by low conversions and excessive production of unwanted by-products as is disclosed in U.S. Pat. No. 2,392,875.

It has been proposed to make phenyl acetate and biphenyl from benzene and acetic acid in the liquid phase in the presence of palladium acetate and without added molecular oxygen by a stoichiometric reaction in CHEM. AND IND., Mar. 12, 1966, page 457.

U.S Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently the preparation of phenyl esters and phenols by the reaction of benzene, molecular oxygen and a lower aliphatic carboxylic acid in the presence of a catalyst composed of a Group VIII metal (U.S. Pat. No. 3,642,873) or a compound of such metal (U.S. Pat. No. 3,651,127) have been disclosed. Similarly, variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type because of problems of catalyst elution, etc. are disadvantageous for an industrial process. U.S. Pat. No. 3,772,383 describes a liquid phase reaction using a very complex catalyst system which includes the use of nitric acid and a lower aliphatic carboxylic acid such as acetic, propionic, n-butyric, isobutyric, or caproic acid. U.S. Pat. No. 3,644,486 describes the catalytic manufacture of oxacylation products and optionally hydroxylation products of condensed aromatic compounds, saturated aliphatic or cycloaliphatic carboxylic acids and molecular oxygen in the presence of a noble metal of sub-group 8 of the Mendeleeff Periodic Table or compounds thereof. This patent also discloses that transition metals can be used with the Group 8 metals and that carbonates or acylates of alkali or alkaline earth metals may also be used as activators in the catalyst system. Although liquid phase reaction is disclosed, no mention is made of the necessity for the use of a hydrocarbon solvent or the removal of water from the reaction mixture is disclosed and extremely low yields of the acetoxylation product are shown.

Generally speaking, these prior art processes deal for the most part with vapor phase oxidation reactions, or liquid phase reactions in which all the reactants (except oxygen in some instances) are initially included in the reaction mixture and they use lower alkyl carboxylic acids such as acetic acid and propionic acid. Moreover, in general the prior art catalytic processes have produced low conversions, usually less than 10%, with poor selectivity to the desired aryl ester, and the hydroxy aromatic compound, such as phenol or naphthols, is often a primary product. The use of the lower saturated carboxylic acids, primarily acetic acid, in the catalytic oxidation process produces a highly corrosive system which can cause reaction equipment corrosion problems and excessive recycle costs as well as the extremely poor conversions and selectivities mentioned above. None of the prior art methods disclose the continuous addition of the aromatic hydrocarbon, the continuous removal of water from the reaction mixture as it forms, nor do they disclose or suggest the use of a solvent or the applicants' catalyst for the higher aromatic compounds in applicants' process.

SUMMARY OF THE INVENTION

We have discovered an improved oxidation process for the transformation of higher aromatic hydrocarbons containing 10 or more carbon atoms and two or more aromatic rings per molecule such as naphthalene, anthracene, biphenyl, phenanthrene, terphenyls, fluorene, and the like, molecular oxygen and a higher carboxylic acid to the corresponding aromatic carboxylate in high conversions and selectivities to the desired product by including a solvent for the aromatic hydrocarbon compound in the process. Our process also is based on the use of a mono or poly-carboxylic acid having 5 or more carbon atoms and a catalyst system composed of a compound of palladium, a compound of antimony and a compound of an alkali metal or an alkaline earth metal.

Our liquid phase reaction produces high conversions and substantially quantitative yields of higher aryl esters when the higher aromatic hydrocarbon is either reacted with carboxylic acid in the presence of an inert solvent or is continuously added in solution in an inert solvent to the reaction mixture during the entire course of the reaction and the solvent is preferably continuously removed from the reaction mixture during the entire course of the reaction. The solvent can be one which has the ability to remove water by entrainment so that the water formed as the higher aromatic hydrocarbon is converted to ester is continuously removed from the reaction mixture in the process. If water, which is a by-product of the oxidation reaction, is allowed to remain in the reaction mixture, it can cause hydrolysis of the aryl ester to produce aromatic hydroxy compounds which in turn can cause fouling and inactivation of the catalyst.

The catalysts useful in our process are preferably composed of palladium metal or compounds of palladium and usually a palladium carboxylate or convenience in conjunction with an antimony compound, usually an antimony carboxylate and a compound, usually a carboxylate, of an alkali metal or an alkaline earth metal. The catalysts of this invention may be used alone or may be supported on a carrier or support material. Suitable carriers include silica, alumina, carbon, quartz, pumice, diatomaceous earth, and the like and others which are known in the art.

The carboxylic acids useful in our invention include mono and poly-carboxylic acids having from 5 to 30 carbon atoms which correspond to the formula $R(COOH)_n$ wherein n is an integer of 1 to 2 and R is a hydrocarbon group having at least $5-n$ carbon atoms. Most preferred are monocarboxylic acids in which n is 1 and R is an aliphatic hydrocarbon group having from 7 to 19 carbon atoms. Some carboxylic acid anhydride can be included with the carboxylic acid in the reaction if desired.

For the higher aromatic hydrocarbons organic solvents which may be useful for the entrainment and removal of water from the reaction mixture include linear hydrocarbons having the formula $C_nH_{2n+2}$ wherein n is from 4 to 14 such as heptane, pentane, octanes and the like, cyclic hydrocarbons having the formula $C_nH_{2n}$ wherein n is from 4 to 14, and linear and cyclic aliphatic ethers.

The process of this invention produces in the case of naphthalene reactant conversions of the carboxylic acid in the order of greater than 10% with selectivities to the naphthyl ester on the order of 100%. Thus, our process produces desired product in such significant quantities that it is directly competitive with the best of the present day commercial processes for the manufacture of alpha and beta naphthyl esters and the naphthols themselves. The naphthyl esters which can be produced by our process can be readily converted to the corresponding naphthols and the corresponding carboxylic acid by known methods for hydrolysis or pyrolysis. The naphthols are easily recovered by known means and the carboxylic acid, ketene or acid anhydride is readily recycled for further use in the oxidation reaction of this invention.

DESCRIPTION OF THE PREFERRED EMBODIMENT

In a typical reaction according to this invention a solution of naphthalene in heptane and the carboxylic acid are contacted with the catalyst in an oxygen containing atmosphere at a reaction temperature in the range of from about 100° to 300° C. and preferably from about 140° to 200° C. and at from about 1 to 100, preferably 1 to 10 atmospheres and most preferably at or near atmospheric pressure. The molecular oxygen can be oxygen, per se, or any gaseous mixture containing molecular oxygen. For instance, molecular oxygen can be in the form of air for convenience. The catalyst can be in the form of a mixture of $(CH_3COO)_2Pd$, $(CH_3COO)_3Sb$ and $CH_3COOM$ and/or $(CH_3COO)_2M'$, wherein M is at least one alkali metal and M' is at least one alkaline earth metal. The molar ratio of Pd:Sb:M or M' should be in the range of from 1:0.1:0.01 to 1:100:100 and preferably in the range of from 1:0.2:0.2 to 1:40:40. During the reaction the water formed is continuously removed conveniently by entrainment with the organic solvent which is continuously distilled from the reaction mixture as the reaction proceeds. The major reaction product (and in most cases the only product) of the reaction, the naphthyl carboxylate, far exceeds the best yields reported in the prior art with essentially quantitative selectivity as previously mentioned, the naphthyl carboxylate thus obtained can be hydrolyzed if so desired to produce naphthol or naphthols by known means and the carboxylic acid and catalyst can be recycled back into the oxidation reaction.

Because essentially no naphthol is produced in the oxidation process of this invention, it is believed that catalyst activity is maintained for long periods of time under continuous use. The rapid removal of water from the reaction mixture is probably at least partly responsible for the absence of naphthol in the reaction product. The presence of naphthol in the reaction product if it should occur is believed to cause catalyst fouling and resulting short catalyst life. The process of this invention is further illustrated in the following examples.

EXAMPLE 1

The reaction was carried out in a glass reactor furnished with a thermometer, mechanical stirrer, Dean Stark type collector equipped with a reflux condenser and gas and liquid tubes. The reactor was charged with 40 g. of octanoic acid, 10 g. (78 m mols) of naphthalene, 8 g. of heptane, 0.34 g. (1.5 millimols) of $Pd(OAc)_2$ 0.45 g (1.5 m mols of $Sb(OAc)_3$ and 0.15 g (1.5 m mols) of KOAc. Dean Stark Collector was filled with heptane. The reaction was carried out at 170° C. with vigorous stirring for 5 hours. GLC analysis showed that 57 m mols (73% yield) of naphthyl octanoate were produced.

EXAMPLE 2

The procedure of Example 1 was repeated except that 10 g. (78 m mols) of naphthalene were charged initially and then additional 5 g. (39 m mols) were added after 2 hours of reaction time and another 5 g. (39 m mols) were added after the 3rd hour and another 5 g. after the 4th hour. Thus, a total of 25 g. (195 m mols) of naphthalene were used in the reaction. Analysis of the final reaction mixture after the 5 hour reaction period showed the formation of 134 m mols (69%) of naphthyl octanoate (97% alpha-naphthyl octanoate, 3% beta-naphthyl octanoate).

EXAMPLE 3

This experiment, which is outside the scope of the present invention, was a repeat of that given in Example 1 except that no $Sb(OAc)_3$ was used. After 5 hours of reaction it was found that only 5.5 m mols of naphthyl ester was found in the reaction mixture (5%).

EXAMPLE 4

The procedure of Example 1 was repeated except that the catalyst used was composed of 0.67 g. (3 millimols) of $Pd(OAc)_2$, 0.9 g. (3 m mols) of $Sb(OAc)_3$ and 0.66 g. (3 m mols) of $Zn(OAc)_2$ After 3 hours of reaction an additional 5 g. (39 m mols) of naphthalene were added to the reaction mixture. At the end of the 5 hour reaction period the reaction mixture was analyzed and was found to contain 80 m mols of naphthyl octanoate (68% yield).

EXAMPLE 5

The procedure of Example 4 was followed except that 20 g. (156 m mols) of naphthalene were charged in 4 increments during the 5 hour reaction time. GLC analysis showed that 101 m mols of naphthyl octanoate were produced in the reaction.

EXAMPLE 6

The procedure of Example 1 was followed except that 0.17 g. (0.75 m mol) of Pd(OAc)$_2$, 0.23 g. (0.75 m mol) of Sb(OAc)$_3$ and 0.14 g. (0.75 m mol) of CsOAc were used as catalyst and the reaction was carried out only for 3 hours. GLC analysis of the final reaction mixture showed that 24 m mols of naphthyl octanoate formed.

EXAMPLE 7

The procedure of Example 6 was followed except that 0.75 m mol of NaOAc was used in place of the CsOAc. Analysis of the final reaction mixture showed that 17.3 m mols of naphthyl octanoate had formed.

EXAMPLE 8

The procedure of Example 6 was followed except that 0.75 m mol of LiOAc was used instead of CsOAc. At the end of the reaction 9.9 m mols of naphthyl oxtanoate were found to be present in the reaction mixture.

EXAMPLE 9

The procedure of Example 1 was repeated except that 0.068 g. (0.3 millimol) of Pd(OAc)$_2$, 2.69 g. (9 m mols) of Sb(OAc)$_3$ and 0.0314 (0.3 m mol) of KOAc were charged as catalyst. The mole ratio of Pd:Sb:K was about 1:30:1. The reaction was carried out at 165±3° C. for 2½ hours. Analysis of the reaction mixture showed that 31 m mols of naphthyl octanoate had formed.

EXAMPLE 10

This Example which is outside the scope of the present invention demonstrates that the lower carboxylic acids are not effective in the oxidation process of this invention. The procedure of Example 1 was followed using 50 g. of acetic acid, 10 g. (78 m mols) of naphthalene, 0.34 g. (1.5 m mols) of Pd(OAc)$_2$, 0.46 g. (1.5 m mols) of Sb(OAc)$_3$ and 0.6 g. (6 m mols) of KOAc. The reaction was carried out for 3 hours at 120°-6° C. (reflux) and oxygen was bubbled through the reaction mixture during the reaction at the rate of 50 cc/min. Analysis of the final reaction mixture showed that less than 1 m mol (less than 2%) of the naphthalene had been converted to naphthyl acetate.

EXAMPLE 11

This Example which is outside the scope of the present invention shows that the absence of an organic solvent in the process of this invention leads to unacceptable results. The procedure of Example 1 was followed except that no heptane or any other organic solvent was employed. At the end of the 3 hour reaction time GLC analysis of the reaction mixture showed that only 1 m mol of naphthyl octanoate and 0.5 m mol of binaphthyl formed.

We claim:

1. An oxidation process for the manufacture of higher aryl esters comprising contacting the reaction mixture of a higher aromatic hydrocarbon selected from the group consisting of naphthalene, anthracene, biphenyl, phenanthrene, fluorene, and terphenyls, an organic solvent, a carboxylic acid and molecular oxygen in the liquid phase at a temperature in the range of from 100° to 300° C. with a catalyst composed of a palladium carboxylate, an antimony carboxylate and a carboxylate of at least one member selected from the group consisting of alkali metals and alkaline earth metals.

2. The process of claim 1 wherein the carboxylic acid is one which corresponds to the formula R(COOH)n wherein n is an integer of from 1 to 2 and R is a hydrocarbon group having at least 5−n carbon atoms.

3. The process of claim 2 wherein n is 1 and R is an aliphatic hydrocarbon group having from 7 to 11 carbon atoms.

4. The process of claim 3 wherein the organic solvent is a member slected from the group consisting of linear hydrocarbons having the formula $C_nH_{2n+2}$, cyclic hydrocarbons having the formula $C_nH_{2n}$ wherein n is an integer of from 4 to 14, and linear and cyclic aliphatic ethers.

5. The process of claim 4 wherein water formed in the oxidation reaction is continuously removed from the reaction mixture by continuous distillation of some of the organic solvent from the reaction mixture.

6. The process of claim 5 wherein the higher aromatic hydrocarbon is naphthalene.

7. The process of claim 6 wherein the organic solvent is heptane.

8. The process of claim 7 wherein the carboxylic acid is octanoic acid.

9. The process of claim 8 wherein the catalyst is composed of a carboxylate of palladium, a carboxylate of antimony and a carboxylate of potassium.

10. The process of claim 8 wherein the catalyst is composed of a carboxylate of palladium, a carboxylate of antimony and a carboxylate of cesium.

11. The process of claim 8 wherein the catalyst is composed of a carboxylate of palladium, a carboxylate of antimony and a carboxylate of sodium.

12. The process of claim 8 wherein the catalyst is composed of a carboxylate of palladium, a carboxylate of antimony and a carboxylate of lithium.

13. The process of claim 8 wherein the catalyst is composed of a carboxylate of palladium, a carboxylate of antimony and a carboxylate of zinc.

* * * * *